United States Patent [19]
Lundquist et al.

[11] 3,989,913
[45] Nov. 2, 1976

[54] INTRAVENOUS FEEDING PUMP TIMER

[75] Inventors: Ingemar H. Lundquist, Oakland; Leif J. Sundblom, Castro Valley, both of Calif.

[73] Assignee: Valleylab, Inc., Boulder, Colo.

[22] Filed: Oct. 11, 1974

[21] Appl. No.: 514,220

[52] U.S. Cl. .......................... 200/35 R; 128/214 E; 417/12; 74/3.54
[51] Int. Cl.² .......................................... H01H 43/00
[58] Field of Search................. 74/411, 53, 3.54; 417/12; 128/214 E, 214 F; 200/35 R, 39 R, 39 A

[56] References Cited
UNITED STATES PATENTS

| | | | |
|---|---|---|---|
| 2,301,556 | 11/1942 | Maris | 74/53 |
| 3,175,416 | 3/1965 | Rogerson | 74/411 X |
| 3,456,648 | 7/1969 | Lee et al. | 128/214 E |
| 3,456,649 | 7/1969 | Jewett | 128/214 F |
| 3,798,982 | 3/1974 | Lundquist | 74/53 |

*Primary Examiner*—John J. Camby
*Attorney, Agent, or Firm*—Flehr, Hohbach, Test, Albritton & Herbert

[57] ABSTRACT

The present invention relates to a timing device for an intravenous feeding pump, whereby the pump can be set to operate at its regular rate for a predetermined period (preferably up to about 4 hours) and thereafter at a reduced rate just sufficient to keep the needle open. The apparatus comprises a gear train driven by the main drive shaft of the intravenous feeding pump actuator, which drives a setting dial at a considerably reduced speed back to a "0" position. The setting dial is clutched to a final gear of the gear train through a spring slip clutch, so that the setting dial can be set to a desired position without driving the gear train or the gear train continue to drive even though the setting dial is latched in its 0 position. When the control knob is in the active position, means is provided when the setting dial returns to its 0 position to actuate an alarm device, such as a light, or a buzzer, or both, and to switch the power circuit of the drive motor into a reduced motor speed for a "keep-open" rate of feed to the needle.

7 Claims, 4 Drawing Figures

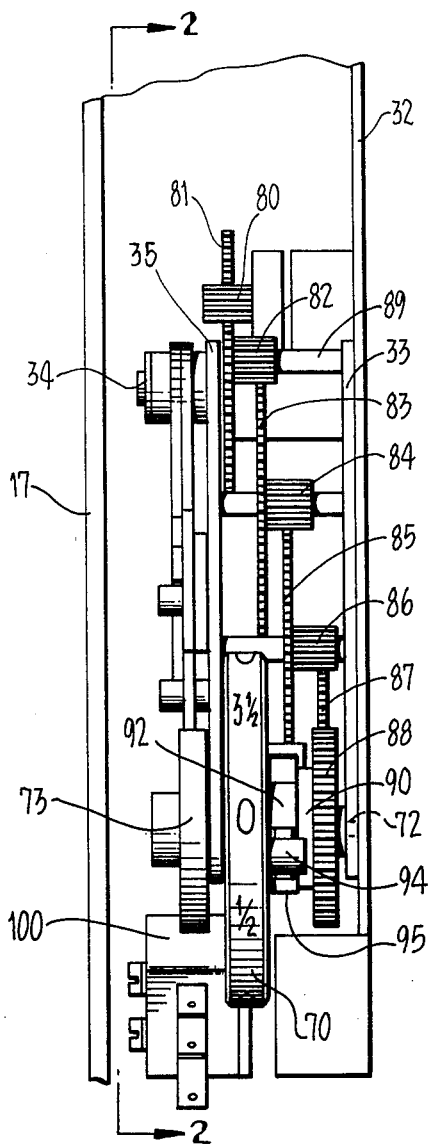
Fig_4
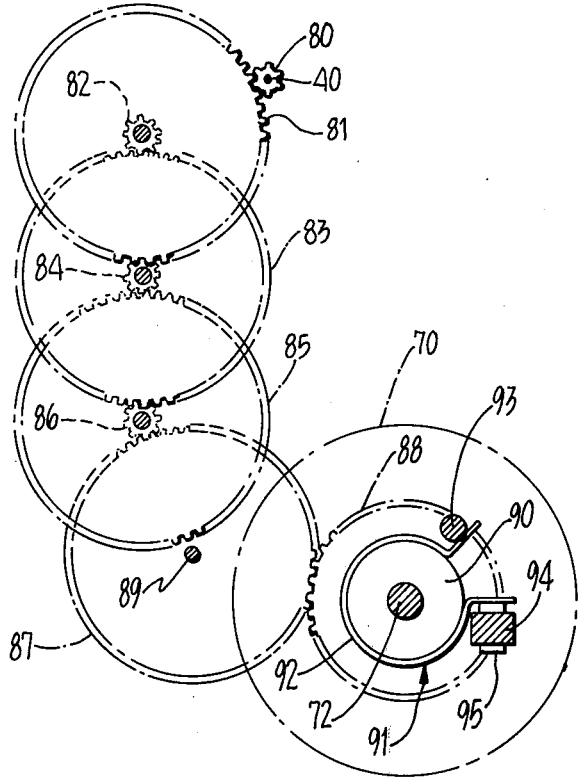
Fig_2
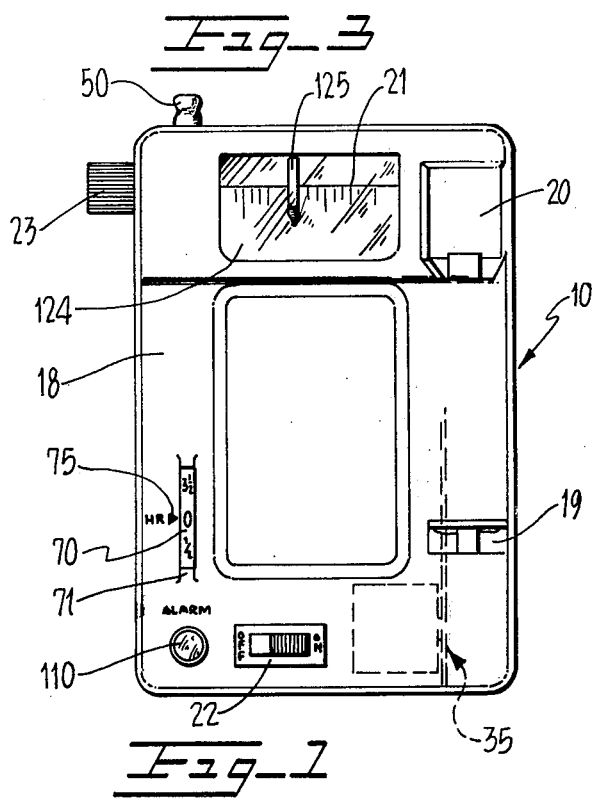
Fig_1

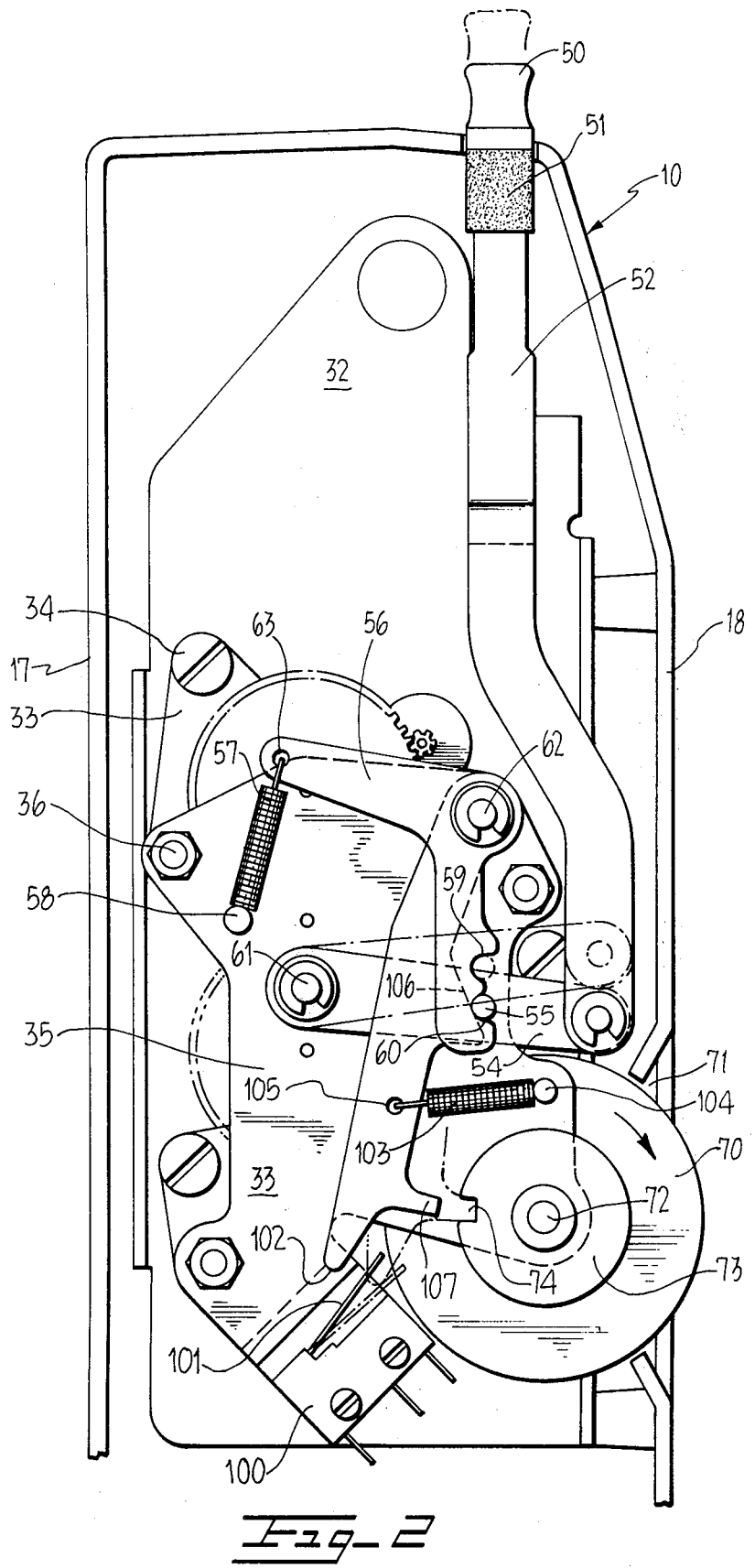
Fig_2

INTRAVENOUS FEEDING PUMP TIMER

BACKGROUND OF THE INVENTION

In recent years there has been a considerable effort spent in the design and fabrication of a suitable intravenous delivery pump that is positive in its operation to force intravenous feeding fluid into the blood vessels of a patient. It has been found that the positive pumping of the parenteral fluid has many advantages over the older gravity feed that has been used for many years. Insofar as the present invention is concerned, the advantages of such pumps need not be discussed. It is sufficient to note that several pumps have been proposed and one or two have been accepted by the medical profession. U.S. Pat. No. 3,798,982, issued Mar. 26, 1974, by one of the present applicants, discloses a pump actuator that is adjustable both as to the timing of the pulses of its operation and the length of each pump stroke (hence the amount of fluid to be delivered at each stroke) over a considerable range of values, with a net result that the pumping of parenteral fluid could be modified over a considerable variety of values, such as from 5 to 1,500 milliliters per hour.

The present invention is designed as a timer for the pump actuator disclosed in said patent, so that when it is required it can be set to deliver the parenteral fluid for a particular period of time up to four hours (in the preferred form of the invention). Thereafter, an alarm could be operated to notify the nursing staff that the period of time had expired, or it could be set to stop the pump actuator as by breaking a switch in the power line to the actuator motor. One of the problems of intravenous feeding is the body's natural ability to "seal off" outside substances, in this case the injection needle. Obviously, a doctor wants to avoid inserting a different needle for each injection. However, in order to avoid using many needles, it is necessary to do something to prevent clogging of the bore of the needle. We propose to avoid clogging while maintaining sterile conditions (although using a single injection needle for a prolonged period) by maintaining a "keep open" flow of fluid under such pressure as to keep the neeedle open, but at a greatly reduced rate of flow. Preferably, the actuator is driven by a two-speed motor in which the power drive has a specific speed for normal operation, such as 10 r.p.m., and an auxiliary speed of approximately one-tenth that value. In this preferred form the motor is automatically switched from the preferred operating speed to a speed of one-tenth that amount when the predetermined time has elapsed, and an alarm is actuated (for example, a warning light is operated, but a signal could be sounded at the nurses station). This form provides that after the selected period of time is expired, the pump will continue to operate at the reduced rate so as to prevent clogging of the needle that has been inserted into the patient's veins.

OBJECTS

It is an object of the present invention to provide a timing device for an intravenous feeding pump actuator which is operative to operate the pump at a predetermined dosage rate for a set period and thereafter to operate at a much lower rate (for example, one-tenth of the normal operating rate) to give a continuous slow injection of parenteral fluid into the patient to prevent clogging of the intravenous needle through which the fluid is injected into the patient.

These and further objects of the invention will be apparent from the description and claims which follow, in which:

DRAWINGS

FIG. 1 shows a front view of a suitable intravenous feeding pump actuator.

FIG. 2 is a left side view of the actuating device taken from a vertical plane just inside the left side of the casing in which the mechanism is contained, such as along the plane indicated by the line 2—2 of FIG. 3.

FIG. 3 is a cross-sectional view of the mechanism shown in FIG. 2 and showing particularly the gear train, the setting dial which is normally driven by the gear train, and the slip clutch which permits operation of the gear train without movement of the setting dial, or vice-versa.

FIG. 4 is a front view of the mechanism shown in FIG. 2.

The apparatus of the present invention is shown in connection with the pump actuator disclosed in the patent abovementioned as indicated in FIG. 1. Such a pump actuator 10 is enclosed in a casing preferably formed of a molded front cover 18 and a rear cover 17 (see FIG. 2). On the exterior wall of the front cover plate 18 is a mounting bracket 19 for supporting the intravenous feeding pump, and an upper bracket 20 which holds the pump in a proper position. Operation of the actuator is controlled by manipulation of a suitable electric switch 22. The amount of fluid to be delivered at each stroke of the pump and the number of strokes per minute is controlled by the manipulation of a setting knob 23 which is effective to position the driving mechanism of the actuator in any of the selected volumetric positions. In the patent above disclosed, this actuator comprises a cam follower arm, not shown in this application, which is set in operating relationship to any one of 20 cams (likewise not shown in this application), which are provided with different cam rises, whereby the operating arm is operated a selected number of times per minute. The length of each stroke with respect to each cam is controlled by means not here pertinent and therefore not shown. However, it can be noted that the setting is instantly viewable through a window 21 in the front cover of the device, which discloses a scale 124 and a pointer 125. This actuator is driven by a suitable motor, which in this invention is a two-speed type in which the slower speed is approximately one-tenth of the regular speed. The parts heretofore mentioned are all shown in the patent above-mentioned and are mentioned only to serve as a background of the present device.

The setting of the present camming device is controlled by the operation of the setting knob 50 (FIGS. 1 and 2). Preferably, only half of the knob 50 extends above the top cover of the pump actuator, the lower half of the knob 50 being painted a distinguishing color, such as a brilliant red, and normally lying within the cover (FIG. 2). It can be noted that the setting knob, as shown particularly in FIG. 2, is in its lowermost, or inoperative, position. However, when the knob 50 is raised to initiate operation of the timer of this invention, the colored section 51 will show and thus tell all members of the staff that the timer is operating. The knob is rigidly secured to the upper end of a setting link 52 by any suitable means, such as a pressure fit. The lower end of the setting link 52 is supported on a pin 53 by which the link 52 is pivotally connected to a support link 54. Supporting link 54 preferably is pivotally mounted on a pivot stud 61 that is affixed to an outside auxiliary frame plate 35. The auxiliary frame plate 35, in turn, is supported by an inside frame plate 33, by suitable spacing studs, such as 36. All of the mechanism of the present invention can be mounted in the auxiliary frame comprised of the frame plates 33 and 35, and their spacing studs 36. This auxiliary frame is adapted to be affixed to the left frame plate 32 of the actuator of the pump above-mentioned by any suitable means, such as studs 34. The supporting link 54 carries a latch pin 55 which is adapted to engage latching notches 59 and 60 formed in the vertical arm of a latching bellcrank 56 that is rotatably mounted on the outside frame plate 35 by any suitable means, such as stud 62. Bellcrank 56 is strongly biased in a counter-clockwise direction by a suitable spring 57 tensioned between a stud 58 on the outside frame plate 35 and a seat 63 at the end of the horizontal end of the bellcrank 56. It is believed obvious that the spring 57, which biases the latching bellcrank 56 in a counter-clockwise direction, will normally restrain the main setting link 52 in its lowermost position through the engagement of pin 55 with the lower notch 60 of the horizontal arm of the bellcrank. However, when the knob 50 is raised, the setting link 52 is held in the upper position by the registration of the pin 55 with the upper notch 59.

The time for which the present timer is set is controlled by a manually operated setting dial 70 (see FIG. 2) which is viewable through an aperture 71 in the front cover plate 18 of the pump actuator. The setting dial is pinned to, or otherwise rigidly mounted on, a short axle, or stud, 72, the ends of which are rotatably mounted in the auxiliary frame plates 33 and 35. Also rigidly mounted on the short shaft 72 is a latching disk 73 (see also FIG. 4) which has a latching notch 74 (see FIG. 2) on its peripheral edge adapted to be engaged by a nose 107 of a switch adjusting arm 102, to be described hereafter. The "0" position of the manually set dial 70 is indicated by a suitable pointer 75 (see FIG. 1) on the outer face of the front cover 18, which pointer is also effective to indicate the time which the timer has left to run (if the device is operative as a timer).

A constantly operating gear train (best shown in FIG. 3) comprises a series of reducing gears which includes a small gear 80 affixed to the left-hand end of the main drive shaft. This gear meshes with a larger gear 81 having an integral small gear 82 which, in turn, meshes with a large gear 83 having an integral small gear 84, which smaller gear 84 meshes with a large gear 85 having a smaller gear 86 integral therewith, and the gear 86 meshes with a larger gear 87 — all as shown in this figure. In the preferred form of the invention, the gear 80 mounted on the main drive shaft 40 has six gear teeth, while the large gears 81, 83, 85 and 87 all have 60 teeth. The small integral gears formed on the hub of the large gears above-mentioned, namely, the gears 82, 84 and 86, have eight teeth each. All of these gears are mounted on short axles or studs 89 journalled in the frame plates 33 and 35. The gear 87 drives a gear 88 which is pivotally mounted on the shaft 72 upon which the setting dial 70 is also mounted. In the preferred form of the present invention, this gear 88 has 43 teeth. It will be obvious that the gear train, beginning with gear 80 on the drive shaft 40 and ending with the gear 88 rotatably mounted on shaft 72, provides a speed reduction of 1:3023, so that if the main drive shaft is driven at an operating speed of 10 r.p.m., the gear 88 will make 4/5 of one revolution in 4 hours, or turn through an angle of 72° for each hour.

The gear 88, which is the final gear in the gear train above described, has a wide hub 90 (see FIGS. 2 and 4) which is embraced by a spring clutch 91 as shown in FIG. 3. The clutch 91 can be formed by a curved leaf spring 92, one end of which engages a stud 93 carried by the setting dial 70, and the other end of which engages a set screw 95 threaded into a nut 94 also affixed to the dial 70. By this means the force of the spring 92 upon the hub 90 of gear 88 can be readily adjusted. The leaf spring 92 should engage the hub 90 with sufficient force to cause the turning of the gear 88 (clockwise in FIG. 3) to resiliently turn the setting dial 70 in the same direction.

It can be noted here that the dial 70 is set from the 0 position by rotating it upwardly in FIG. 1, or counter-clockwise in FIGS. 2 and 3, until the predetermined selected time registers with the pointer 71 carried by the actuator cover. Then, when the actuator is operated, the gear 80 drives the gear train, including the gear 88, to return the dial to its 0 position.

It has been mentioned that the time herein described is effective to preferably change the speed at which the motor is driven, but it could be used to completely shut off the power to the motor, or to operate an alarm, such as lamp 110 (FIG. 1). In the preferred form of the invention, the return of the dial to its 0 position is effective to both operate the alarm system, such as lamp 110, and to automatically change the speed at which the motor operates the drive shaft 40 from its normal operating speed of 10 r.p.m. to a value of approximately one-tenth of that figure. This is a preferred form of construction, so that there will be a slow flow of parenteral fluid injected through the pump at longer spaced intervals to prevent clogging of the intravenous needle. This apparatus is controlled by a suitable switch 100 (see FIG. 2). In the preferred form of the invention, the switch 100 is provided with a single leaf 101 in one position of which (the full line position as shown in FIG. 2) the switch controls the full power to the motor (not shown) for its operation at its regular speed to drive main drive shaft 40 at its normal rate of 10 r.p.m. In its other position (the dotted line position shown in FIG. 2), the flow of power enables the motor to operate at only one-tenth that speed. Movement of the leaf 101 from the full speed posiion to the reduced speed position is controlled by a rockable arm 102 that is pivotally mounted on the stud 62. This arm is strongly biased (counter-clockwise in FIG. 2) into engagement with the latching disk 73 by a strong tension spring 103 tensioned between a stud 104 on the outside auxiliary frame plate 35 and a spring seat 105 formed in the arm 102. Intermediate the extremities of the arm 102, in the plane adapted to lie opposite the latching pin 55 on supporting link 54, the arm 102 is provided with a cam face 106 which, when the setting knob 50 and its supporting link 52 are in the lowermost position shown in FIG. 2, holds the arm 102 away from the periphery of the latching disk 73. However, when the knob 50 and its supporting link 52 are lifted to enable operation of the device, the pin 55 is lifted away from the cam face 106, so that arm 102 is moved into engagement with the periphery of the latching disk 73 by the force of spring 103. When the setting dial 70 has been set to a selective value position and the control knob 50 is lifted to enable operation of the device, a nose 107 formed on the forward edge of the control arm 102, will ride upon the periphery of the disk 73 until the notch 74 comes into registration with that nose 107. When the nose 107 registers with the notch 74, the arm 102, from the force of spring 103, will be pulled counter-clockwise and the nose 107 will fall into the notch. Such registration of the nose 107 in the notch 74 will lock the dial 70 and the disk 73, and at the same time the tip of the arm 100 will engage leaf 101 of switch 100 and move it to the slower speed position. At the same time it is preferred that the alarm, such as the light 110 shown in FIG. 1, will be operated to indicate to personnel that the time has expired and further action is therefore necessary. If it is desired to continue feeding at the reduced rate, no change need be made. However, if full feeding of fluid is desired, the control knob 50 is depressed, whereupon link 52 moves link 54 and its pin 55 downwardly to cause the pin 55 to cam arm 102 away from disk 73 (to the full line position in FIG. 2). The switch will return to its high speed position and the pump will again be operative at its set rate. While the pump is so operating, the gear train 80 to 88 will continue to drive the dial 70. However, such rotation of the dial is meaningless since the control knob 50 is down.

It is believed that operation of the present device will be understood from the disclosure preceding. However, it can be briefly summarized that in the normal condition of the pump actuator 10, the knob 50 will be in its retracted position shown in FIG. 2. In this position the switch cotnrol arm 102 is held away from the latching disk 73 by the pin 55 engaging cam face 106, as shown. If it is desired to operate the actuator 10 for a limited time, the dial 70 is rotated to select the time desired. Since normally a limited time only is desired, the preferred form of the present invention is limited to four hours of use, which will normally be much more than sufficient for medical purposes. After the dial 70 has been properly set, the knob 50 is lifted, which will display the signal section 51 thereof above the cover of the actuator 10. The lifting of the link 52 lifts the pin 55 away from the cam face 106 of switch control arm 102, so that arm 102 is released to the force of its spring 103. Thereupon the nose 107 will ride upon the periphery of the latching disk 73. Then, when the operation of the actuator is started, the gear train shown in FIG. 3, including gears 80 to 88, inclusive, will slowly rotate the setting dial 70 (clockwise in FIGS. 2 and 3 and downwardly in FIGS. 1 and 4) until the nose 107 can fall into the notch 74. When this occurs, arm 102 drops, under the force of its spring 103, engaging leaf 101 of switch 100 and changing the setting from the normal operating speed to the slow speed at approximately one-tenth of the rate previously set. At the same time the alarm is operated, so that when a nurse or other operator answers the alarm, it will be immediately indicated to them that the time has expired. Thereupon the operator can take whatever action is necessary in the circumstances.

It is believed that many modifications of the present invention can be made in minor matters, but the extent of scope of the present invention is believed apparent from the specification above and the claims which follow.

What is claimed is:

1. In a timing device for an intravenous feeding pump, a two-speed motor having one speed which is a normal speed and another speed which is a speed substantially lower than the normal speed, a main drive shaft driven by said motor, a rotatable and settable dial for indicating the time the device is to be operative, a reducing gear train driven by said main drive shaft and operable to rotate said settable dial in one direction, switch means electrically connected to the motor for controlling the flow of power to said motor and having first and second operative positions and in the first position causing said motor to operate at its normal speed and in the second position causing said motor to operate at the lower speed, a movable member operative upon return of said setting dial to its 0 position to operate said switch means to move the same from the first to the second operative position and a control member movable from a position at which it disables said movable member to a position in which said movable member is operative upon return of said setting dial to its 0 position.

2. The device of claim 1 indicating means for indicating when the control member is in a position to enable operation of said movable member.

3. The apparatus of claim 1 wherein said gear train includes yieldable drive means.

4. The apparatus of claim 1 comprising also a signalling device operated by the change of the switch means from said first operative position to said second opertive position.

5. In a timing device for an intravenous feeding pump actuator, a two-speed motor having a higher speed and a slower speed, a drive shaft driven by said motor, a settable dial for selectively determining the length of time the actuator is to be operated at regular speed, a two-positioned power switch electrically connected to said motor, in one position of which the two-speed motor is operated at its higher speed and the other of which the motor is operated at its slower speed, a movable member adapted to operate said power switch, means on said movable member for sensing when the settable dial is returned to its 0 position and thereupon operate said power switch to move the same from its said one position to said other position, a gear train driven by said motor for moving said manual setting member in a direction to return it to its 0 position and manual means for enabling and disabling said movable member.

6. The apparatus of claim 5 wherein the gear train includes a yieldable clutch and wherein the movable member latches the settable dial in its 0 position.

7. In a timing device for an intravenous feeding pump actuator, a two-speed motor having a higher speed and a slower speed, a drive shaft driven by said motor, a manually settable member for selectively determining the length of time the actuator is to be operated at regular speed, a two-position power switch electrically connected to said motor, in one positon of which the two-speed motor is operated at its higher speed and the other of which the motor is operated at its slower speed, a movable member adapted to engage said settable member, means on said movable member for sensing the 0 position of the settable member, a gear train driven by said drive shaft for moving said manually settable member in a reverse direction to return it to its 0 position, a resilient connection between said gear train and said manually settable member, whereby the gear train can be actuated even though the setting member is latched in a 0 position, means operated by movement of said movable member in sensing a 0 position of said manually settable member and operative to change the setting of said switch from its higher speed position to its slower speed position and manual means for disabling said movable member.

* * * * *